United States Patent [19]
Donovan

[11] Patent Number: 5,979,300
[45] Date of Patent: Nov. 9, 1999

[54] STARTER CULTURE RECEPTACLE AND METHODS USING THE SAME

[75] Inventor: John P. Donovan, Springbrook, Australia

[73] Assignee: Kefir Culture Natural Limited, Paddington, Australia

[21] Appl. No.: 08/731,048

[22] Filed: Oct. 9, 1996

Related U.S. Application Data

[63] Continuation-in-part of application No. 08/345,407, Nov. 21, 1994, abandoned, and a continuation-in-part of application No. PCT/AU95/00353, Jun. 19, 1995.

[30] Foreign Application Priority Data

Jul. 27, 1994 [AU] Australia ................................. PM7010
Nov. 28, 1994 [AU] Australia ................................. PM9703

[51] Int. Cl.$^6$ .............................. A47G 19/14; C12M 3/00
[52] U.S. Cl. ........................ 99/323; 206/0.5; 422/265; 422/276; 435/304.1
[58] Field of Search ................................. 99/323; 206/0.5; 426/7, 8, 34, 43; 422/261, 265, 276; 435/283.1, 304.1

[56] References Cited

U.S. PATENT DOCUMENTS

| 453,972 | 6/1891 | Gray ........................................... 99/323 |
| 2,291,060 | 7/1942 | Schiess ..................................... 99/323 |
| 5,076,425 | 12/1991 | Plone ....................................... 99/323 |

*Primary Examiner*—David A. Redding
*Attorney, Agent, or Firm*—Nixon & Vanderhye PC

[57] ABSTRACT

A receptacle for a fermented milk product starter culture is disclosed. The receptacle allows a single batch of starter culture to be transferred from one quantity of fermented milk to a fresh quantity of milk for formation of additional fermented milk product. Methods for the production of fermented milk product are also disclosed.

2 Claims, 3 Drawing Sheets

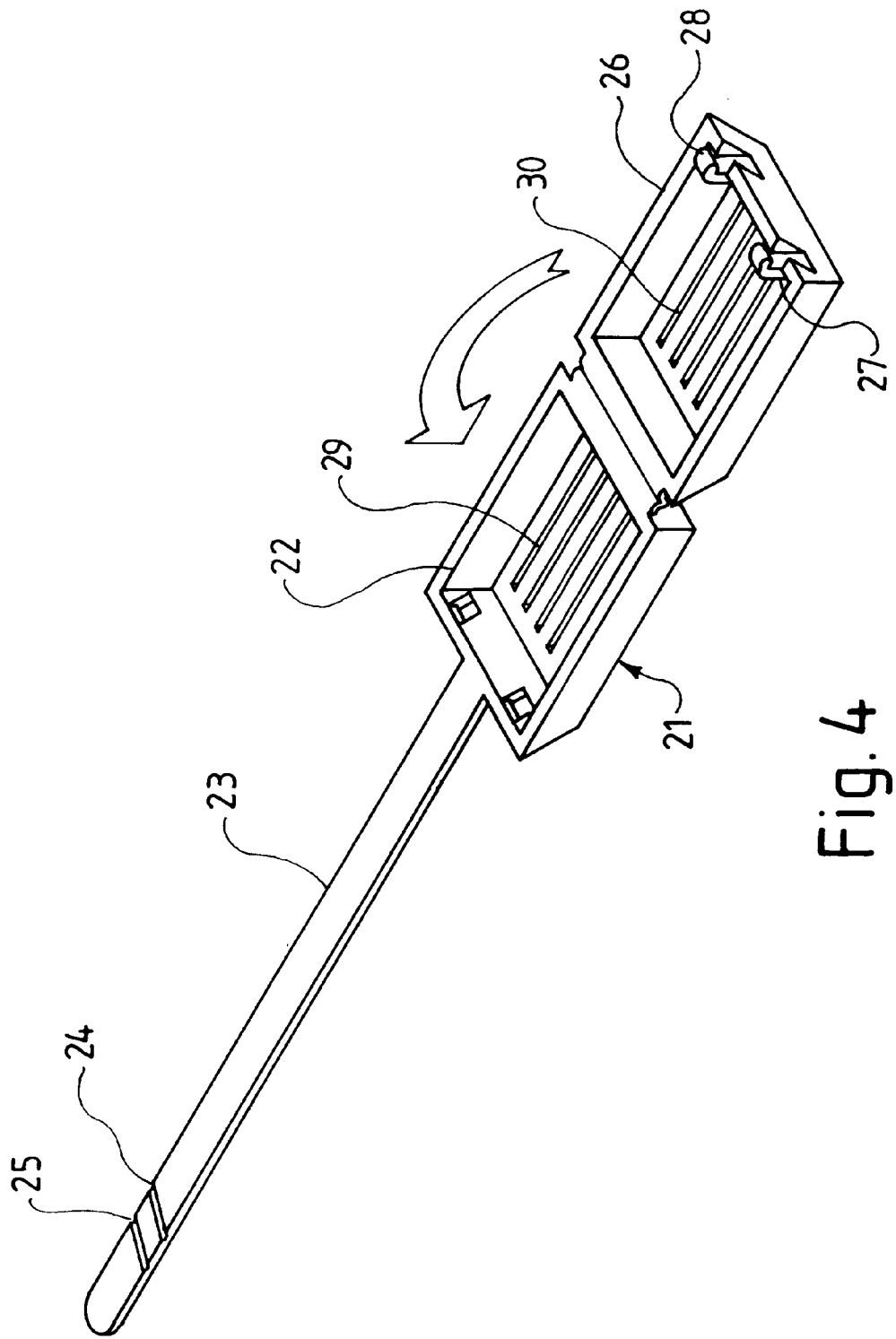

STARTER CULTURE RECEPTACLE AND METHODS USING THE SAME

This is a continuation-in-part of application Ser. No. 08/345,407, filed Nov. 21, 1994, now abandoned, and is a continuation-in-part of PCT/AU95/00353, filed Jun. 19, 1995.

This invention relates to a device for use in making fermented milk products and methods of making such products utilising the device. Methods of making kefir and yoghurt using the device are given as particular examples of the invention but it will be appreciated that the invention is suitable for making any fermented milk product. In particular, the invention relates to methods for the home manufacture of fermented milk products.

BACKGROUND ART

Fermented milk products have been known for centuries. Such products include sour cream, buttermilk, kefir, koumis and various cheeses.

Yoghurt is a fermented milk product which has been known for over a thousand years. The product is believed to have originated in Asia where Turkish nomads were producing material referred to as "yoghurt" by the 8th century AD.

While the nutritive value of yoghurt is primarily determined by the milk from which it is made, yoghurt has the advantage that it is more easily digested than milk. Furthermore, yoghurt has therapeutic value and is used in treatment of intestinal disorders, liver and bile disorders and in the topical treatment of skin and oral disorders.

Yoghurt is therefore a product with considerable market appeal and processes are available for large scale production. However, there is also interest in home production of yoghurt, particularly when a product not available commercially is desired.

In home production, the usual process followed is to precook milk, cool to an incubation temperature, and add a yoghurt culture. Generally, a fresh yoghurt culture is used with each batch of milk.

Yoghurt cultures are known which comprise microorganisms aggregated with an inert material. Such cultures can be used to prepare yoghurt from a first batch of milk then transferred to a second batch of milk for conversion to yoghurt followed by a further transfer and so on.

A portion of yoghurt produced from a first batch of milk can also be used as a starter culture for a second batch of milk. Further transfers can be made but eventually portions will become ineffectual as starter cultures.

Home production of yoghurt may be facilitated by using a process which includes the step of transferring an aggregated starter culture or portion of yoghurt to additional batches of milk. However, devices or systems for facilitating such transfers are not known.

SUMMARY OF THE INVENTION

It is an object of this invention to provide a device which may be used in kefir and yoghurt making processes and processes for making other fermented milk products which involve transfer of starter cultures.

In one aspect, this invention provides a receptacle for a starter culture for a fermented milk product, said receptacle having a plurality of openings in a wall thereof, wherein said openings are sized to prevent egress of aggregated fermented milk product-forming micro-organisms retained within the receptacle and to limit egress of fermented milk product formed in the receptacle but which at least allow passage of milk and free fermented milk product-forming micro-organisms.

The term "starter culture" includes free as well as aggregated micro-organisms. The term also includes a portion of fermented milk product which contains fermented milk product-producing micro-organisms.

The term "fermented milk product" includes products which are sometimes referred to as "cultured milk products".

The receptacle can be any shape and is dimensioned and configured as appropriate for the container of the milk which is to be fermented. The receptacle can range in shape from a compact "bullet-shaped" article to a member having an elongate tubular shape.

In particular embodiments of the invention, the receptacle is advantageously fabricated from a material which allows the receptacle to float on the surface of milk with at least a portion of the receptacle below the surface. To aid buoyancy, an externally projecting member can be provided around the receptacle to support the receptacle on the surface of the milk.

The receptacle can also be used submerged in the milk in which case the receptacle is advantageously fabricated from a material having a density greater than that of milk. For ease of retrieving a submerged receptacle, and/or for position the receptacle within the milk, the receptacle can have associated therewith a member extending from the receptacle to above the surface of the milk. Typically, the member is a flexible member such as a chain, or a rod or strip of plastics material. Receptacles fabricated from a material having a density greater than that of milk are preferably fabricated from stainless steel or a high density plastics material.

The receptacle can also be used with a milk-containing vessel of dimensions such that the receptacle is supported by the neck of the vessel. If present, the externally projecting member around the receptacle can be used to support the receptacle in the vessel.

The openings in the receptacle, as well as allowing milk to contact the starter culture, also allow a fluid such as water to be flushed through the receptacle. This can be advantageous to reduce the amount of set yoghurt or other fermented milk product in the receptacle prior to transfer of the receptacle to a fresh volume of milk. This will be explained in greater detail below. The openings also allow the passage of free fermented milk product-forming micro-organisms.

The receptacle preferably has a lid to facilitate charging the receptacle with starter culture and cleaning the receptacle. Advantageously, the lid has a plurality of openings. The openings in the lid, in conjunction with the openings in the receptacle, still allows fluid to be flushed through the receptacle.

The receptacle can have a cover over the top thereof which also covers the lid in embodiments which include a lid. The cover advantageously includes a lip adjacent the point of contact between the receptacle and the cover. The lip can serve as a support when the receptacle is mounted in the neck of a vessel or can aid buoyancy when the receptacle is floating on the surface of milk.

If the receptacle includes an externally projecting member, that member and the lip of the cover are preferably co-planar.

The lid and cover can be secured to the receptacle by any suitable means. Such means include threaded engagement, engagement of tabs in corresponding slots, or mere friction engagement. The preferred engagement means is a snap fit between the lid and the receptacle, and the cover and the receptacle.

The cover and receptacle lid are typically circular with the receptacle having a circular cross section. Preferably the receptacle is an inverted cone or inverted truncated cone.

The openings in the receptacle and lid can be any shape. Preferably, the openings are slots, the walls of which are advantageously angled inwardly towards the interior of the receptacle. In embodiments where the lid is circular, the slots can be radially disposed with respect to the centre of the lid, or concentrically disposed thereto. Similarly, in the preferred form of the receptacle, the slots can be radially or concentrically disposed with respect to the centre of the circle at the truncated end of the cone whereas on the curved surface of the cone, the slots are typically concentric with respect to the axis of the cone or lie on a line projecting from the apex of the cone. The width of slots is typically between about 0.3 mm and about 1 mm.

The receptacle and cover typically comprise a plastics material. A preferred material is ABS/polypropylene co-polymer. The receptacle can also be fabricated from a metal. A preferred metal is stainless steel.

As indicated above, in some embodiments the receptacle is an elongate tubular member. Such members typically comprise an elongate tube having a plurality of holes disposed generally along the length thereof and having closed ends. The holes in the tubular member are large enough to allow milk to come into contact with starter culture. Typically, holes are of about 1 mm in diameter.

Advantageously, receptacles comprising a tubular member include at least one sealable opening therein to allow the receptacle to be charged with starter culture. A sealable opening typically comprises an end of the tube which is sealed by a plug fitted into, or a cap fitted over, the end. Alternatively, the tubular member can comprise at least two interconnectable sections which when separated provide openings to the tube sections. The interconnection can be any suitable manner of connection such as a snap fit or a threaded connection.

Tubular receptacles are advantageously constructed from flexible food-grade plastic tubing or the like. Such receptacles can be bent or twisted to be adapted to the dimensions of the container with which they are used. Alternatively, tubular receptacles can be fabricated from a non-flexible material such as a plastics or metal material. Typical dimensions for a flexible tubular receptacle are about 45 cm long by about 14 mm OD. However, tubular receptacles of about 14 mm OD can be up to about 100 cm in length.

A tubular receptacle when charged with starter culture is particularly suited for introduction into a commercially available container of milk for production of yoghurt or fermented milk product. Such containers are typically two liter plastic bottles of milk or 20 liter plastic bags of milk but can be any other suitable volume of milk in a container that is able to be re-sealed. The charged tubular receptacle is entirely immersed in the milk for formation of fermented milk product. Once incubation is complete, the tubular receptacle can be removed, rinsed under running water then placed into a new container of milk.

In a second aspect, this invention provides a method of making a fermented milk product, the method comprising the steps of:

1) contacting a volume of milk with a receptacle having a plurality of openings in a wall thereof and inoculating said milk with fermented milk product forming micro-organisms, wherein said inoculation is by adding said micro-organisms directly to the milk or by adding said micro-organisms via said receptacle, and wherein said openings in said receptacle are sized to limit egress of fermented milk product formed in the receptacle but which at least allow passage of milk and free fermented milk product-forming micro-organisms;

2) incubating said volume of milk to allow fermented milk product formation; and 3) transferring said receptacle containing fermented milk product to a fresh volume of milk and incubating same to allow fermented milk product formation.

The method according to the second aspect can further comprise repetition of step (3).

Micro-organisms which can be used in step (1) of the method according to the second aspect are well known in the art. For example, Streptococcus and Leuconostoc species are used for sour cream and buttermilk production while *Lactobacillus bulgaricus* can also be used for Bulgarian buttermilk production. Streptococcus species are predominantly used for cheese production often in conjunction with other species such as Penicillium, Brevibacterium or Lactobacillus species. For yoghurt production, micro-organisms used include Lactobacillus species such as *L. bulgaricus* or *L. acidophilius* or streptococci such as *Strep. thermophilus* or *Strep. lactis*. For making kefir, a typical starter culture comprises a mixture of *Strep. lactis, Strep. cremoris,* several yeast species and other lactic acid bacteria.

As indicated above, in step (1) of the method according to the second aspect, inoculation can be effected by adding micro-organisms directly to the milk or by adding the micro-organisms via the receptacle. That is, micro-organisms can first be placed into the receptacle and the receptacle then contacted with the milk to effect inoculation. The micro-organisms used as an inoculum can be provided in a portion of fermented milk product. For example, a portion of set yoghurt containing viable micro-organisms can be used as the inoculum.

Suitable incubation conditions are well known in the art.

At transfer, the fermented milk product in the receptacle can be diluted or reduced in volume by flushing the receptacle with a fluid such as water.

In a third aspect of the invention, there is provided a method of making a fermented milk product, the method comprising the steps of:

1) charging a receptacle having a plurality of openings in a wall thereof with a composition of aggregated micro-organisms capable of fermented milk product formation; and 2) contacting a volume of milk with the charged receptacle from step (1) and incubating said milk to allow fermented milk product formation.

In a fourth aspect of the invention, there is provided a method of making a fermented milk product, the method comprising the steps of:

1) charging a receptacle having a plurality of openings in a wall thereof with a composition of aggregated micro-organisms capable of fermented milk product formation;

2) contacting a volume of milk with the charged receptacle from step (1) and incubating said milk to allow fermented milk product formation; and 3) transferring said receptacle to a fresh volume of milk and incubating same to allow fermented milk product formation.

The method according to the fourth aspect can further comprise the repetition of step (3).

The methods according to the second to fourth aspects of the invention can advantageously be used for making yoghurt or kefir.

A preferred composition of aggregated micro-organisms for use in the third and fourth aspects of the invention when used for making kefir is Bug 01 which has been deposited with Australian Government Analytical Laboratories under accession number N94/53565. Another composition of micro-organisms which may be used in the methods according to the third and fourth aspects of the invention is the stabilised preparation of Lactobacillus cells described in Japanese Specification JP04330274.

The milk used in the methods according to the second to fourth aspects of the invention can be any milk suitable for making fermented milk products and includes milk from buffalos, cows, mares, goats, yaks and reindeers as well as milks made from beans, grains, seeds or nuts. The milk can be processed milk such as skim milk or lactose-reduced milk.

It will be appreciated that the receptacle used in the method of the second to fourth aspects includes all the variations and preferments of the receptacle according to the first aspect. It will also be appreciated that the use of the receptacle according to this invention allows the simple transfer of a starter culture from one batch of fermented milk product to a fresh batch of milk. In the case of the second aspect, a portion of fermented milk product is transferred while in the case of the third and fourth aspects, the composition of aggregated micro-organisms is transferred.

Transferring the starter culture allows a number of batches of product to be prepared from a single initial inoculum. In the case of Bug 01, the starter culture can be transferred an indefinite number of times.

The composition used to charge the receptacle in the method of the third and fourth aspects can be in the form of a powder, in a granulated form, in the form of tablets, or comprise micro-organisms immobilised on an inert support. Powdered or pelletised composition can be provided in a milk soluble container such as gelatine capsules. Alternatively, the composition can be provided as aggregated dried material such as can be produced by freeze drying.

In a fifth aspect, this invention provides a kit for making a fermented milk product, the kit comprising a) a receptacle for a starter culture, the receptacle having a plurality of openings in walls thereof to allow milk to contact said starter culture; and b) a starter culture comprising a composition of aggregated micro-organisms capable of forming a fermented milk product.

The receptacle defined in part (a) of the fifth aspect has all the variations and preferments described above for the first aspect of the invention.

The composition according to part (b) of the fourth aspect is preferably provided in a container. Such containers include the containers specified above as well as cellulose capsules and foil sachets.

Methods according to the invention are conveniently used for producing comestibles. However, the fermented milk products of the methods also have non-comestible uses. In particular, fermented milk products according to the invention can advantageously be used as the principle ingredient, or at least a component of, a skin-care or hair-care composition.

Thus, according to a sixth aspect of the invention, there is provided a method of preparing a composition for the treatment of skin or hair, said method comprising the steps of:

1) preparing a fermented milk product using a method according to any one of the second, third or fourth aspects of the invention; and 2) combining fermented milk product from step (1) with at least one other component selected from a plant extract, a preparation of plant tissue, an antiseptic, an astringent, a cleansing agent, an emollient, an exfolient, minerals, vitamins, protein, a pH modifier, a thickener, or a diluent.

Specific components suitable for use in compositions prepared using the foregoing method will be known to those of skill in the art. For example, plant extracts include herbs, spices and essential oils. Typical of the foregoing suitable for use in the method of the invention include fennel, comfrey, cowslip, cucumber, elderflower, marigold, violet, witch hazel, almond oil, apricot oil, lavender oil, olive oil, peppermint essence, or sunflower oil, Preparations of plant tissue include homogenates of fruit, vegetable or seed tissue, such as homogenates of apricot, avocado, lemon, orange, peach or tomato. The preparation can be an homogenate of flesh of fruit or vegetable matter, or a preparation of the skin of a fruit or vegetable. Another typical preparation of plant tissue is a cereal preparation such as oatmeal.

Plant extracts or preparations of plants can also serve as antiseptics, astringents, cleansing agents, emollients, exfolients, pH modifiers or as sources of vitamins and/or minerals. For example, elder tree flowers contain an oil which acts as an astringent, lemon juice has antiseptic and exfoliating properties, oatmeal serves as a cleansing agent, almond meal has emollient properties, cider vinegar can be used as a pH modifier, avocado and apricot kernels are good sources of vitamin D and vitamin E respectively, while potato is rich in potassium.

Examples of other materials which can serve as components in preparations made by the method according to the sixth aspect are seaweeds such as kelp as a source of minerals, honey as a source of vitamins and potassium, brewer's yeast as a source of B group vitamins and the minerals phosphorus and potassium, and clays such as Fuller's earth as astringents.

The various aspects of the invention will now be exemplified. A starter culture receptacle will be exemplified with reference to the accompanying drawings briefly described hereafter.

BRIEF DESCRIPTION OF THE DRAWINGS

FIGS. 3 and 4 are perspective views of further starter culture receptacles according to the invention.

BEST MODE AND OTHER MODES OF CARRYING OUT THE INVENTION

Preferred forms of apparatus according to the invention will now be exemplified followed by examples illustrating methods according to the invention.

EXAMPLE 1

Starter Culture Receptacle

Figure 1:
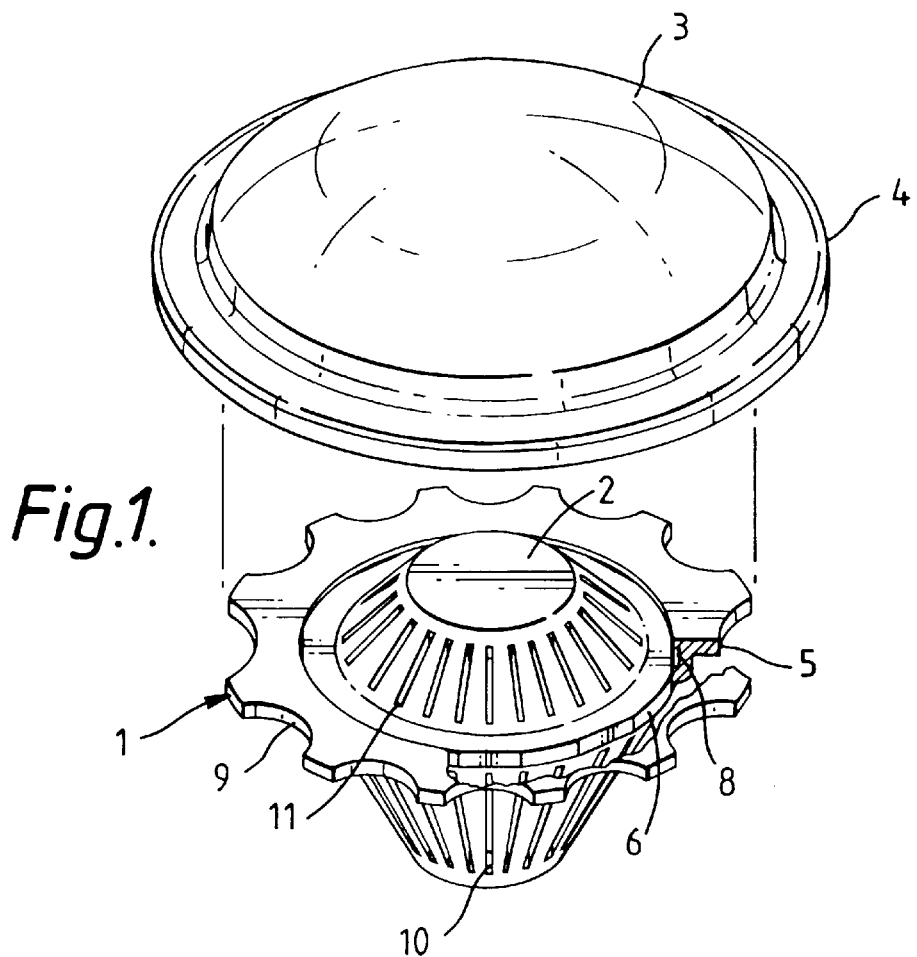
FIG. 1 is an exploded perspective view from above in partial break-away of a receptacle and cover.
Figure 2:
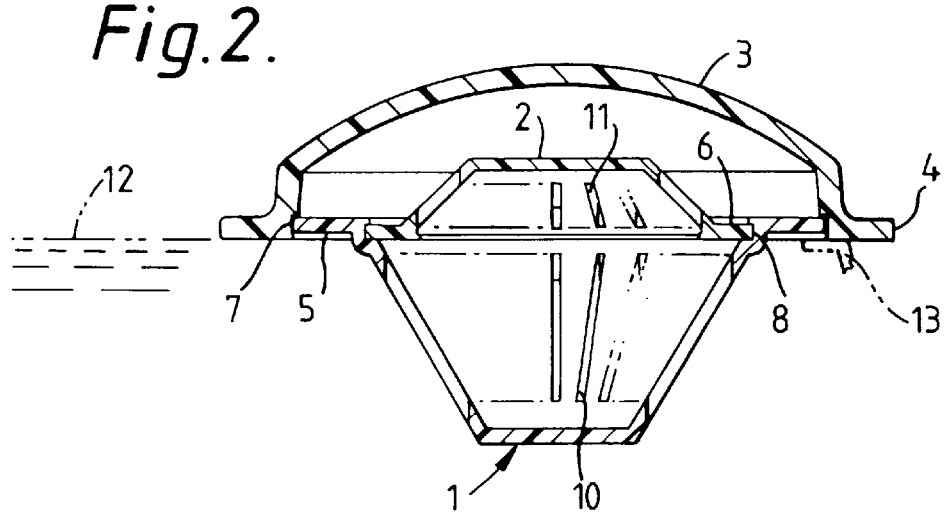
FIG. 2 is an elevational view in cross-section of the receptacle and cover shown in FIG. 1.

Referring to FIGS. 1 and 2 in which like numbers indicate the same component, there is shown receptacle 1 having a lid 2. The receptacle is covered by a dome-shaped cover 3 which has a lip 4 at the edge thereof which contacts the receptacle.

Receptacle 1 is in the general shape of an inverted truncated cone the base of the cone forming an opening into which lid 2 fits. An annular projection 5 adjacent the base of the cone engages cover 3. Lid 2 similarly has the shape of a truncated cone and has an annular projection 6 from the edge of the lid engages the receptacle.

Annular projections 5 and 6 engage grooves 7 and 8 in cover 3 and receptacle 1 respectively as a snap fit. Annular projection 5 preferably has semi-circular cut outs as shown at 9 of FIG. 1.

In the example depicted in the drawings, slots are only provided in the curved surface of the receptacle and lid as indicated at 10 and 11 respectively. The alternative modes of using the receptacle are shown in FIG. 2. The receptacle is shown floating on the surface of milk at 12 or supported on the neck of a vessel at 13. The receptacle depicted in the drawings is dimensioned to be used with 300 ml plastic milk bottles.

The cover, lid and receptacle depicted in the drawings are injection moulded from ABS/PP co-polymer. The receptacle has dimensions of 48 mm wide at annular projection 5 and 24 mm high with the lid in situ. Cover 3 has a maximum diameter of 60 mm and a height of 12 mm. Slots are about 1 mm wide at the outer surfaces of the receptacle and lid tapering to about 0.35 mm at the inner surfaces of the receptacle and lid.

EXAMPLE 2

Starter Culture Receptacle

Figure 3:
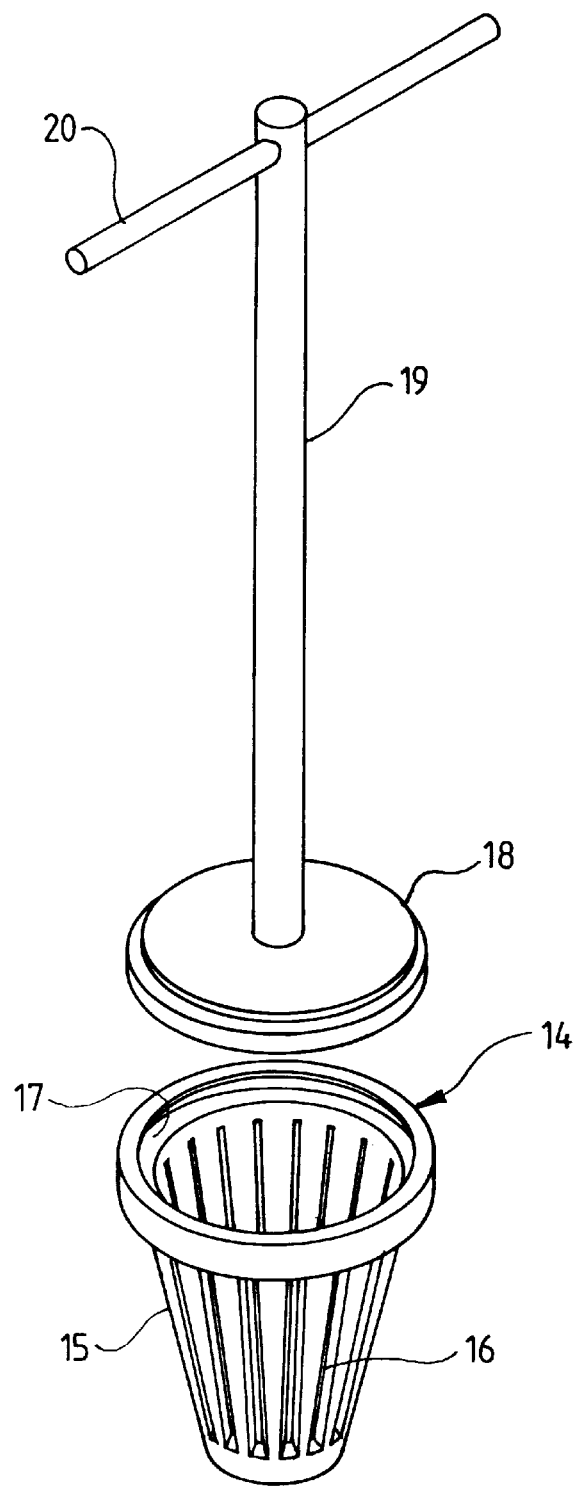

FIG. 3 depicts a starter culture receptacle adapted for immersion in a container of milk while suspended from the neck of the container. The figure shows receptacle 14 which includes a chamber 15 which is an inverted truncated cone. The conical wall of the chamber has a plurality of slots therein, one of which is indicated at 16. The open base 17 of the chamber is adapted to receive a lid 18 as an interference fit. A member 19 extends from the lid, which member is axially aligned with conical chamber 15 when the lid 18 is in situ. Member 19 has a cross-piece 20 at the end distal the lid.

Chamber 15 has dimensions of about 22 mm long with a maximum diameter of 20 mm. Member 19 and cross-piece 20 are about 70 mm and 32 mm long, respectively. Slots 16 in chamber 15 are about the same width as the slots of the receptacle shown in FIGS. 1 and 2 (see Examples 1 above). Receptacle 14 is fabricated from high density polypropylene.

It will be appreciated by one of skill in the art that receptacle 14 is dimensioned to fit into a milk container having a neck diameter of about 30 mm. Containers having such neck diameters are commonly available in the US as one gallon plastic bottles. In use, the cross-piece is fitted into the bottle cap and the cap screwed onto the bottle. This immerses the chamber in the milk where the starter culture held in the chamber can ferment the milk.

It will also be appreciated that the cross-piece can merely rest against the rim of the neck of the bottle. Furthermore, a cap can be fused directly to rod 19 so that the cap becomes the cross-piece.

EXAMPLE 3

Starter Culture Receptacle

FIG. 4 depicts yet another type of receptacle which is within the scope of the invention. The figure shows receptacle 21 comprising a tray-like chamber 22 having an elongate member 23 extending therefrom. The elongate member has adjacent transverse fold lines 24 and 25 near the end of the member distal the chamber. The fold lines allow the member to be bent to form a hook for securing the receptacle to the rim of a container of milk.

With further reference to chamber 22, this can be covered by a hinged lid 26, as shown generally by the arrow. Clips 27 and 28 are provided to hold the lid closed. Lid 26 is essentially a mirror image of chamber 22 and the bottoms of the trays comprising the chamber and lid include pluralities of slots as indicated at 29 and 30.

Chamber 22 has overall dimensions of about 22 mm long by about 15 mm wide. Elongate member 23 has a length of about 60 mm and a width of about 4 mm. Receptacle 21 is fabricated from high density polypropylene.

In use the chamber portion of the receptacle containing starter culture is placed into the milk in a container of the same. The hook formed in member 23 is then used to hang the receptacle from the rim of the container. The member can also be used to retrieve the receptacle from the container.

The member can include a preformed hook rather than a formable hook being provided via the fold lines.

In variants of the receptacle depicted in FIG. 4, lid 26 is dispensed with and covering provided by a foil or plastic sheet welded to the rim of chamber 22. Starter culture is of course added to the chamber prior to welding of the sheet to the chamber.

Receptacles as described above in this example can also be manufactured in linear arrays comprising a plurality of receptacles. The individual receptacles in an array are linked by frangible webbs or tabs.

EXAMPLE 4

Preparation of Kefir

A receptacle having a volume of about 15 ml and generally as depicted in FIGS. 1 and 2 was charged with about 1 g of Bug 01 as freeze-dried granules. The receptacle was positioned in the neck of a container holding approximately 300 ml of pasteurised cows milk so that milk contacted the granules within the receptacle. The milk was then allowed to stand at room temperature for 24 h at which time it was noted that the milk had been converted to kefir.

The receptacle was removed from the kefir rinsed under cold running water to remove excess kefir leaving Bug 01 granules. The rinsed receptacle with granules was then positioned in a fresh batch of milk and allowed to stand as before with kefir formation resulting.

This process was repeated at least 50 times with good quality kefir produced from each batch of milk.

The experiment was repeated using lesser amounts of Bug 01—down to 0.2 g—with equal efficacy.

EXAMPLE 5

Preparation of Yoghurt

A receptacle as used in Example 1 was charged with about 5 g of Jalna biodynamic yoghurt. The charged receptacle was positioned in the neck of a container holding approximately 300 ml of pasteurised cows milk so that the milk contacted the yoghurt in the receptacle. The milk was allowed to stand as in Example 4 after which the milk was converted to yoghurt.

The receptacle was removed from the yoghurt and rinsed with running tap water to remove excess yoghurt from the exterior of the receptacle. The rinsed receptacle containing yoghurt was then positioned in a fresh batch of milk. After standing at room temperature for 24 h, yoghurt was formed.

The process described in the previous paragraph was repeated with yoghurt again being formed.

EXAMPLE 6

Use of a Tubular Receptacle

In this example, use of a tubular receptacle for production of fermented milk product is described.

A tubular receptacle having dimensions of approximately 45 cm in length and approximately 14 mm OD was charged with about 15 g of a fresh preparation of Bug 01. The charged receptacle was placed into a 20 liter plastic bag of full cream cows milk so that the receptacle was fully immersed in the milk. The bag was re-sealed and allowed to stand at room temperature for 24 hours by which time fermented milk product had formed. The receptacle was removed and rinsed under water and placed into a fresh container of milk. The fresh container of milk was incubated as above and fermented milk product was again formed. This process was repeated fifteen times using the same tubular receptacle charged with the initial portion of Bug 01.

Other milks can be substituted for the pasteurised milk used in the above examples. These milks include full cream cows milk, soya milk (plain or with additives such as VITASOY™), goats milk, low fat milk or skim milk. Other starter cultures can also be used such as commercially available yoghurt starter cultures or fresh cultures of Bug 01.

It will also be appreciated that differing incubation conditions can be used, such as standing the milk at a higher temperature or initially warming the milk prior to inoculation. The time that the inoculated milk is allowed to stand can be varied to give products of differing consistency.

The following examples illustrate the use of kefir produced by the method detailed in Example 4 as the basis of skin and hair treatment preparations. The efficacy of such preparations is due in part to the fact that kefir cleanses the skin and balances skin pH. Unless otherwise noted, preparations are used within 7 days of preparation.

EXAMPLE 7

Moisturisers

Avocado and Kefir Moisturiser

| Components: | 1 avocado |
| --- | --- |
| | 1 teaspoon of honey |
| | 1 teaspoon of lemon juice |
| | kefir |

The avocado, honey and lemon juice are blended to a thick paste. Sufficient kefir is added to form a stiff cream which is refrigerated for at least 30 minutes. For use, the moisturiser is massaged onto the face until the cream disappears. The cream is left on the face overnight and cleaned off next morning.

Herb and Kefir Lotion

Many herbs are useful in the prevention of wrinkle formation. These include fennel, comfrey, cucumber and cowslip flowers.

| Components: | fennel |
| --- | --- |
| | kefir |

The fennel is finely chopped and mixed with enough kefir to make a smooth paste. This is left stand for an hour to allow the fennel juices to mix with the kefir. (Any of the above mentioned herbs can be added instead of the fennel). The paste is applied as a face mask, left on for 15 minutes and splashed off with tepid water.

Kefir Night Cream (for oily skin)

| Components: | 2 tablespoons of kefir |
| --- | --- |
| | 1 egg yolk |
| | 1 tablespoon of honey |
| | 1 tablespoon of cream |
| | ½ tablespoon of cider vinegar |
| | ½ tablespoon of tomato juice |

The kefir, egg yolk and cream are mixed. The cider vinegar and tomato juice are then added and mixed well. The honey is warmed and added to the other ingredients and whisked well. The preparation is used on the face at night. If the preparation is too drying on the skin, more cream can be used in preparing the mixture.

Elderflower and Kefir Lotion

| Components: | 4 teaspoons of kefir |
| --- | --- |
| | 2 teaspoons of elderflower infusion (prepared by adding 15 g of herbs to 500 ml of boiling water which is allowed to stand for 5 minutes before straining) |
| | 1 teaspoon of apricot oil |
| | 2 teaspoons of almond oil |

The components are placed in a sealed glass container and mixed well by shaking. The preparation can be used day or night as a moisturiser for normal to dry skin.

Kefir and Marigold Lotion

| Components: | 2 teaspoons of kefir |
| --- | --- |
| | 2 teaspoons of apricot oil |
| | ½ teaspoon of almond oil |
| | 1 teaspoon of marigold infusion (prepared by adding 30 g of marigold flowers to 500 ml of boiling water which is allowed to cool but not strained) |

All other ingredients are combined in the marigold infusion and mixed well. A day or night lotion is provided which assists in balancing the skin's acid mantle.

Almond and Kefir Cream

| Components: | 2 tablespoons of almond meal (ground almonds) |
| --- | --- |
| | 150 g of kefir |

The components are mixed well and immediately applied to the face where it can be left for about an hour then rinsed off with warm water. This preparation is particularly useful for dry or blemished skin.

Cucumber and Kefir Soother

| Components: | 1 small cucumber |
|---|---|
| | 100 g of kefir |

The cucumber is sliced, combined with the kefir and mixed using a blender. The preparation must be refrigerated for an hour before use. The preparation can be used on the face and neck where it is preferably left overnight.

EXAMPLE 8

Masks

Oatmeal and Kefir Mask

| Components: | ½ cup of uncooked oatmeal |
|---|---|
| | 250 g of kefir |

This mask is suitable for treating skin having enlarged pores. The ingredients are mixed together and refrigerated for at least 10 hours. To use the mask, the face is first steamed using a bowl of hot water containing rosemary leaves. A towel may be placed over the bowl and head to retain the steam. The steaming process opens the pores after which the mask can be applied and left on the face for about an hour after which it is rinsed off.

Kefir and Peach Mask

| Components: | 1 large ripe peach, skinned |
|---|---|
| | 1 teaspoon of honey |
| | kefir |

The peach is cut into chunks, blended for a brief time and the honey added. Sufficient kefir is added to make a preparation having a creamy, spreadable consistency. The preparation can be prepared by hand if a blender is not available. If a thicker consistency is desired, a little oatmeal can be added.

Kefir Clay Pack for Oily Skin

| Components: | 2 teaspoons of kefir |
|---|---|
| | 12 teaspoons of fuller's earth |
| | 2 teaspoons of potato water (prepared by boiling potatoes in water and straining out the potatoes to produce the potato water) |

The ingredients are blended until a smooth paste is formed. The preparation is applied to the cleansed face, avoiding the eyes, where it is left for about 20 minutes. The preparation is rinsed off with remaining potato water. The face is then dried and moisturised using any suitable moisturiser. The mask is suitable for use with oily, troubled skin but should not be used more than twice a week.

Peppermint Kefir Mask

| Components: | 1 tablespoon of fuller's earth |
|---|---|
| | 120 g of kefir |
| | 1 teaspoon of honey |
| | 3 drops of peppermint essence |
| | 1 pinch of bicarbonate of soda |

The kefir is mixed with the fuller's earth then added to the other ingredients. The preparation is applied to the face and neck using cotton balls to assist with the application. The mask is left on the face for about 30 minutes then rinsed off with luke warm water. The mask counteracts oiliness.

Tomato and Kefir Mask

| Components: | 3 ripe tomatoes (sieved with only the juice used) |
|---|---|
| | 120 g of kefir |
| | 50 g of oatmeal |

The oatmeal is boiled in a little water for about 20 minutes. The tomato juice and kefir are mixed together then stirred into the cooled oatmeal to make a smooth paste. The paste is applied to the face and neck where it is left for about 30 minutes then rinsed off gently with tepid water. This mask is suitable for oily skins and blackheads.

EXAMPLE 9

Cleansing Scrubs

Orange Kefir Cleansing Scrub

| Components: | 1½ tablespoons of kefir |
|---|---|
| | 1 tablespoon of safflower oil |
| | 1 tablespoon of grated orange peel |
| | 1 tablespoon of oatmeal |

All ingredients are mixed together to form a paste. The paste is applied to the face and massaged in using circular movements. The eye area should be avoided. The paste is rinsed off with warm water and the face patted dry. The scrub can be used once a day for oily skins or twice a week for drier skins.

Kefir and Yeast Scrub

| Components: | 1 tablespoon of kefir |
|---|---|
| | 2 teaspoons of almond meal |
| | 1 teaspoon of brewer's yeast |
| | 1 teaspoon of runny honey |
| | 2 drops of lavender oil |

The ingredients are mixed and massaged gently into the face, after which the scrub is rinsed off with lukewarm water. This scrub should not be used if there are broken veins on the cheeks. The brewer's yeast stimulates circulation and this can aggravate an existing condition.

EXAMPLE 10

Cleansing Lotions

Violet and Kefir Lotion

| Components: | 2 tablespoons of fresh or 1 tablespoon of dried violet flowers and leaves |
|---|---|
| | 150 ml of boiling water |
| | 150 ml of kefir |

The boiling water is poured over the violets and the infusion allowed to cool. The cooled infusion is filtered through filter paper or some other suitable filter means. The filtered liquid is then added to the kefir, mixed thoroughly and refrigerated. The lotion can be used over several days and is suitable for use with spotty skin.

Honeyed Kefir Cleansing Cream

| Components: | 16 tablespoons of kefir |
| --- | --- |
| | 5 tablespoons of washed elderflower heads |
| | 2½ tablespoons of melted honey |

The kefir and elderflowers are placed in a pot over low heat and simmered for half an hour. The mixture should not be overheated or the kefir will curdle. The mixture is removed from the heat and allowed to stand for about 5 hours. The mixture is then re-heated, the flower heads filtered out and the melted honey added. The cream is prepared by beating together the final components for several minutes. The cream is preferably stored refrigerated. For use, the cream is applied generously over the face and neck and cleaned off with damp cotton wool. The cleanser suits all skin types.

Kefir and Lemon Cleanser

| Components: | 3 tablespoons of kefir |
| --- | --- |
| | 3 teaspoons of freshly squeezed lemon juice |

The cleanser is prepared by whisking the ingredients together. The preparation can be stored in the refrigerator in a suitably sealed container. For cleansing, the preparation is applied to the face and neck and cleaned off with damp cotton wool.

EXAMPLE 11

Preparation for the Treatment of Freckles

Kefir and Oatmeal Paste

| Components: | 4 tablespoons of kefir |
| --- | --- |
| | 2 tablespoons of flaked oatmeal |

The ingredients are mixed into a paste, with more kefir added if required to produce a preparation having an easily spreadable consistency. The paste is spread over freckles and left on for no longer than 20 minutes after which it is washed off with water. Preferably, application of the foregoing preparation is followed by application of a light moisturiser. This treatment can be used daily.

EXAMPLE 12

Preparation for the Treatment of Hands

Almond Kefir Cream

| Components: | 1 tablespoon of almond oil |
| --- | --- |
| | 1 cup of kefir |

The ingredients are mixed well and massaged into the hands at bedtime. Cotton gloves are preferably worn to enhance the treatment. The preparation is washed from the hands the next morning.

EXAMPLE 13

Bath Water Additive

Apricot and Kefir Oil

| Components: | 2 tablespoons of melted butter |
| --- | --- |
| | 2 tablespoons of olive oil |
| | 1 teaspoon of apple cider vinegar |
| | 2 tablespoons of witch hazel |
| | juice of three apricots (prepared using a blender) |
| | 120 g of kefir |
| | 2 beaten eggs |
| | 500 ml of milk |

The butter and olive oil are mixed together and allowed to stand for about 1 hour. The apple cider vinegar, witch hazel, apricot juice and kefir are added with stirring. The eggs and half the milk are next added to the mixture in a blender. After thorough blending, the remaining milk is added. The mixture can be kept refrigerated in a sealed container. A mixture is sufficient for six baths as only a cupful is required per bath.

EXAMPLE 14

Hair Conditioners

Sea Kelp and Kefir Conditioner

| Components: | 1 egg yolk |
| --- | --- |
| | 120 g of kefir |
| | 1 teaspoon of grated lemon rind |
| | 1 teaspoon of sea kelp powder |

The egg yolk is beaten and added to the kefir to which mixture the lemon rind and kelp powder is added. For use, the preparation is massaged into the hair and scalp and left for about 30 minutes. The preparation is rinsed from the hair using a small quantity of lemon juice in the rinse water followed by shampooing if desired.

Kefir Conditioner for Fly-Away Hair

| Components: | 2 tablespoons of kefir |
| --- | --- |
| | 1 egg |

The ingredients are whisked together until thoroughly blended. The conditioner is used after shampooing the hair when it is massaged into the hair over a period of about 5 minutes. The head is then wrapped in a warm towel or a shower cap placed over the head and left for about 15 minutes. The conditioner is rinsed from the hair with warm water.

It will be appreciated that many other changes and modifications can be made to the apparatus and methods exemplified above without departing from the broad ambit and scope of the invention.

MICROORGANISM DEPOSIT

A sample of Bug 01, which is a mixed lactic acid bacteria and yeast culture, was deposited with the Australian Government Analytical Laboratories of 1 Suakin Street, Pymble, New South Wales 2073, Australia on Nov. 8, 1994 and given the accession number N94/53565.

I claim:

1. A buoyant receptacle for a starter culture for a fermented milk product, said receptacle including:

a wall at least in part defining a chamber having the general shape of an inverted truncated cone, a base of the cone forming an opening into which a lid is fitted; and a dome-shaped cover covering said lid and operatively connected to said wall adjacent said opening, said cover having an annular outwardly projecting lip by which said receptacle can be supported, said wall chamber and said lid each having a plurality of slots therein sized to prevent egress of aggregated fermented milk product-forming micro-organisms retained within the receptacle and to limit egress of fermented milk product formed in the receptacle but which allow passage of milk and free fermented milk product-forming micro-organisms.

2. A receptacle for a starter culture for a fermented milk product, said receptacle including:

a wall at least in part defining a chamber having the general shape of an inverted truncated cone, a base of the cone forming an opening into which a lid is fitted; and an elongate member extending outwardly away from said lid and coaxial with the axis of said chamber, and a cross-piece at the end of said elongate member distal from said lid;

said wall having a plurality of slots therein sized to prevent egress of aggregated fermented milk product-forming micro-organisms retained within the receptacle and to limit egress of fermented milk product formed in the receptacle but which allow passage of milk and free fermented milk product-forming micro-organisms.

* * * * *

UNITED STATES PATENT AND TRADEMARK OFFICE
CERTIFICATE OF CORRECTION

PATENT NO.  : 5,979,300
DATED       : November 9, 1999
INVENTOR(S) : Donovan, John P.

Page 1 of 1

It is certified that error appears in the above-identified patent and that said Letters Patent is hereby corrected as shown below:

Column 15,
Line 9, delete "chamber".

Signed and Sealed this

Seventeenth Day of July, 2001

Attest:

*Nicholas P. Godici*

NICHOLAS P. GODICI
*Attesting Officer*   *Acting Director of the United States Patent and Trademark Office*